United States Patent [19]

Hann et al.

[11] Patent Number: 4,863,697
[45] Date of Patent: Sep. 5, 1989

[54] CATALYTIC ALKYLATION APPARATUS

[75] Inventors: Paul D. Hann; Joe VanPool, both of Bartlesville, Okla.

[73] Assignee: Phillips Petroleum Co., Bartlesville, Okla.

[21] Appl. No.: 197,776

[22] Filed: May 17, 1988

Related U.S. Application Data

[62] Division of Ser. No. 756,908, Jul. 19, 1985, Pat. No. 4,777,323.

[51] Int. Cl.$^4$ ............... G05D 23/12; G05D 23/13; G05D 11/02
[52] U.S. Cl. .................... 422/110; 422/108; 422/109; 422/111; 422/112; 436/55
[58] Field of Search ............... 422/108, 110, 111, 112, 422/235, 109, 62; 585/331, 709, 710, 719, 723; 436/55, 147, 148

[56] References Cited

U.S. PATENT DOCUMENTS

3,969,078  7/1976  Zabransky ..................... 436/55
4,205,196  5/1980  Makovec et al. ............... 585/701
4,275,032  6/1981  Anderson ..................... 422/110

Primary Examiner—Michael S. Marcus
Assistant Examiner—D. John Griffith Jr.
Attorney, Agent, or Firm—George E. Bogatie

[57] ABSTRACT

A continuous process for alkylating an alkylatable hydrocarbon in the presence of a acid-type catalyst in which the alkylatable hydrocarbon is contacted with an alkylating agent in the presence of a catalyst in a reaction zone so as to alkylate the alkylatable hydrocarbon. The reaction product is separated in an acid settler vessel into an alkylate product phase, located in the upper portion of the first separation zone, and a catalyst phase located in the lower portion of the first separation zone. The catalyst phase is further separated into a first portion and second portion, such that the first portion is cooled and recycled for use in the alkylation reaction zone as a catalyst recycle, and the second portion is passed into a second separation zone, wherein the catalyst phase is further separated into a rerun catalyst stream containing acid-type catalyst and an acid soluble oil stream. The rerun catalyst stream is passed into the hydrocarbon phase of the acid settler vessel. In order to prevent excessive pressure in the acid settler vessel as a result of the hot rerun catalyst stream, two liquid hydrocarbon drawoffs from the acid settler vessel are employed. The warm upper drawoff of the acid settler vessel is charged as feed to a depropanizer and stripper and the cool lower drawoff of the acid settler vessel is charged as reflux feed to an isostripper. The acid settler vessel contains a pressure controller set to the desired pressure to be maintained in the upper portion of the acid settler vessel. As the pressure in the acid settler vessel increases, a valve connected to the cool lower drawoff is closed and a valve connected to a conduit attached to the warmer upper drawoff is further opened such that an increased amount of hot hydrocarbon is shifted to the isostripper so as to lower the heat in the acid settler vessel thereby maintaining the desired pressure in the acid settler vessel.

7 Claims, 1 Drawing Sheet

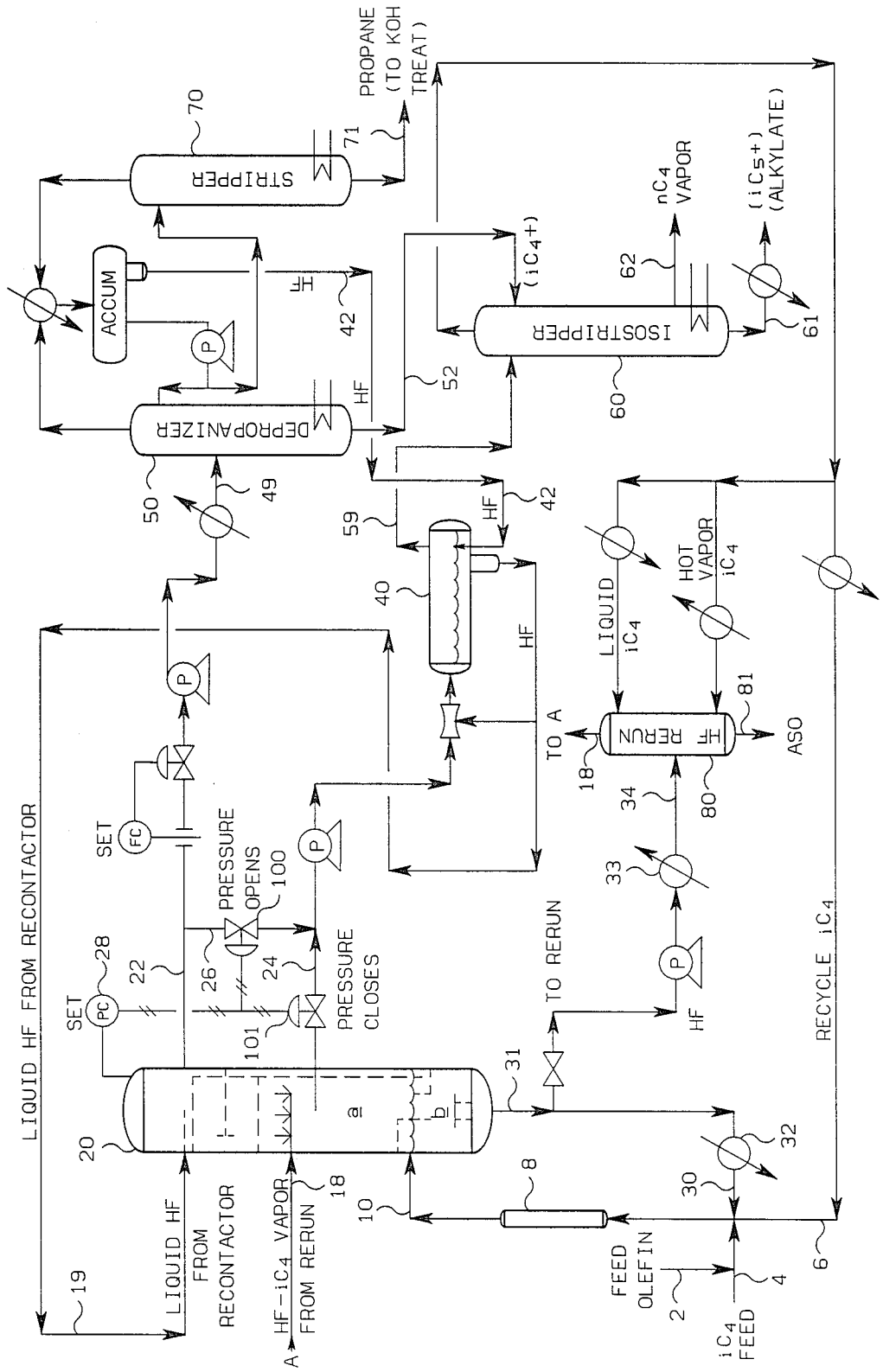

CATALYTIC ALKYLATION APPARATUS

This application is a division of application Ser. No. 756,908 filed July 19, 1985 now U.S. Pat. No. 4,777,323.

The present invention relates to a catalytic alkylation process and apparatus. In one aspect the invention relates to an alkylation system in which cyclic flow of alkylation catalyst is provided. In another aspect the invention relates to an improved method and apparatus for maintaining desired pressure and temperature in a catalyst settler vessel by manipulating the flow rates of two hydrocarbon liquid drawoffs from the catalyst settler vessel.

Numerous processes are known in the prior art for alkylating an alkylatable hydrocarbon with an alkylating agent in the presence of a catalyst. From a commercial standpoint, the most prevalent systems involve the cyclic circulation of an acid-type catalyst, such as hydrofluoric acid, sulfuric acid, etc., through a reaction zone, a separation zone, a cooling zone and back to the reaction zone.

One such process for the alkylation of hydrocarbons, utilizing the cyclic circulation of the acid-type catalyst, introduces the reactant hydrocarbons into the acid catalyst in the lower portion of an alkylation reaction zone maintained at suitable alkylation reaction conditions. A stream comprising catalyst, alkylate product and unconsumed reactants passes from the upper portion of the reaction zone into a catalyst settling zone, wherein separation occurs between the hydrocarbon phase and the catalyst phase. Catalyst is withdrawn from the catalyst phase of the settling zone and passed through a cooling zone and then back into the reaction zone. This part of the system has open communication throughout for a major cyclic catalyst flow. A hydrocarbon stream is withdrawn from the hydrocarbon phase for further processing by fractionation to produce an alkylate product.

It is common for alkylation systems employing acid-type catalysts to include a so-called catalyst "rerun" system through which at least a portion of the catalyst is at least intervally passed to remove therefrom water and acid-soluble oil. The rerun system will normally involve withdrawing a portion of the catalyst phase as it flows from the catalyst settler vessel to the cooler. This withdrawn catalyst phase is heated to a temperature sufficient to cause separation of a liquid phase, comprising predominately acid-soluble oils and some water, and a vapor phase comprising predominately catalyst and unreacted feed materials. The heated catalyst stream is passed into a catalyst rerun fractionating column. Generally a portion of the alkylatable hydrocarbon, in liquid form, is utilized as a reflux and another portion, in gaseous form, is utilized as a stripping medium in the rerun separator. Water and acid-soluble oil is withdrawn as a product from the bottom of the rerun fractionating column while the vapor phase is recycled to the catalyst settler vessel. It is known to inject the vapor phase product of the rerun fractionating column either into the alkylate product phase or into the catalyst phase in the catalyst settler vessel.

High concentrations of propane-propylene, diolefins, sulfur, or water in the feed streams can cause low purity catalyst which requires charging a high volume of catalyst to the catalyst rerun system, thereby increasing the temperature in the catalyst settler vessel with the resulting increase in pressure. Since the alkylation reactor is in a continuous loop with respect to catalyst flow, the introduction of high pressure acid into the reactor requires operation of the alkylate/isobutane fractionator at pressures high enough to allow the recycle isobutane to flow into the reactor. This is costly in higher pressure equipment and high pressure steam for reboiler duty.

Butadiene or other impurities present in the feed can result in higher rates of formation of acid-soluble oils in the alkylation reaction. The higher concentrations of acid-soluble oils in the alkylation reaction effluent requires correspondingly higher throughputs in the rerun tower, which in turn results in more hot catalyst phase than can be injected into the hydrocarbon phase of the catalyst settler. It is desirable that part of the hot catalyst phase (acid and isobutane vapor) be passed into the alkylate product phase of the catalyst settler vessel in order to (1) minimize organic fluorides, (2) utilize heat from the hot catalyst phase (to maintain pressure), and (3) to avoid use of an external cooler to remove the heat from the hot catalyst phase (such a cooler could require expensive equipment, such as Monel). The heat of vaporization (condensation of acid and vapor isobutane) is absorbed by the hydrocarbon (alkylate product phase) in the acid settler.

It would therefore be highly desirable to provide a means for controlling the amount of hydrocarbon liquid withdrawn from the alkylate product phase of the catalyst settler vessel, so as to control the pressure and/or temperature in the catalyst settler vessel.

It is therefore an object of the invention to provide an improved process and apparatus for the alkylation of hydrocarbons. A further object of the present invention is to provide an improved process and apparatus for the alkylation of hydrocarbons, utilizing a cyclic flow of an acid-type catalyst. Another and further object of the present invention is to provide a means for controlling the withdrawal of liquid hydrocarbon from the catalyst settler vessel, so as to control the pressure and temperature in the catalyst settler vessel.

These and other objects and advantages of the invention will be apparent from the following detailed description of the invention.

SUMMARY OF THE INVENTION

In accordance with the present invention, there is provided an improved alkylation process for preventing an increase in pressure and/or temperature beyond a desired range in the liquid hydrocarbon phase in a catalyst settler vessel, by controlling the flow rates of hydrocarbon liquid stream withdrawn from upper and lower liquid drawoffs in the catalyst settler vessel. The process involves passing the resulting effluent, from a mixture of an alkylatable hydrocarbon, alkylating agent and acid-type catalyst in an alkylation reaction zone, into a catalyst settler vessel, so as to separate the alkylation reaction zone effluent into an alkylate product phase, located in the upper portion of the catalyst settler vessel, and a catalyst phase containing acid-type catalyst and acid-soluble oil, located in said lower portion of the catalyst settler vessel, and withdrawing from the upper portion of the catalyst settler vessel an alkylate product stream and first and second portions of the separated catalyst phase from the lower portion of the catalyst settler vessel. The first portion of the separated catalyst phase is cooled and recycled for use in the alkylation reaction zone as a catalyst recycle. The second portion of the separated catalyst phase is passed into a second separation zone, wherein the catalyst phase is separated to obtain a rerun catalyst stream comprising predominantly acid-type catalyst and alkylating agent. The rerun catalyst stream is passed into to the alkylate product phase located in the upper portion of the catalyst settler vessel. In order to prevent high pressure in the catalyst settler vessel, which can occur when too high of a rate of rerun catalyst enters the catalyst settler vessel, two hydrocarbon liquid drawoffs from the catalyst settler vessel are employed so as to remove more hot hydrocarbon liquid and less cool hydrocarbon liquid from the catalyst settler vessel as the pressure tries to increase in the catalyst settler vessel. The hot upper hydrocarbon liquid drawoff is charged as feed to a depropanizer and the cool lower hydrocarbon liquid drawoff is charged as a reflux feed to the isostripper, with the hot vapor rerun catalyst stream from an acid rerun vessel entering the catalyst settler vessel between the drawoffs.

In the present invention, the isoparaffin hydrocarbon, when referred to herein, will be referred to as the "alkylatable hydrocarbon" while the olefinic hydrocarbon will be referred to herein as the "alkylating agent".

BRIEF DESCRIPTION OF THE DRAWINGS

The drawing is a simplified flow diagram of an alkylation system in accordance with one embodiment of the present invention.

DETAILED DESCRIPTION OF THE INVENTION

The present invention can be carried out in any type of reactor system utilizing a cyclically flowing, acid-type catalyst. The preferred system in accordance with the present invention is a cyclic catalyst system in which the mixture of hydrocarbon feed materials is maintained in a liquid state. Such a system using HF catalyst is described in detail in U.S. Pat. No. 3,213,157, which is incorporated herein by reference.

Conventionally, the alkylation reaction can comprise the reaction of an isoparaffin, such as isobutane, with an olefin or other alkylating agent such as propylene isobutylene, butene-1, butenes-2 and amylenes, reaction of a normal paraffin with an olefin or other alkylating agent or the reaction of an aromatic hydrocarbon with an olefin or other alkylating agent. It has been found that the reaction of an isoparaffin with a $C_4$ olefin, such as isobutylene, butene-1, and/or butenes-2 is an example of a preferred reaction involving these specified materials and mixtures thereof. One preferred mixture is an isoparaffin and a typical mixed "butene" produced from a catalytic cracking operation, which will comprise about 25.0 percent by volume of butene-1, about 30.0 percent by volume of isobutylene and about 45.0 percent by volume of butenes-2.

A variety of alkylation catalysts can be employed in the alkylation reaction, including well known acid catalysts such as sulfuric acid, hydrofluoric acid, phosphoric acid; metal halides, such as aluminum chloride, aluminum bromide, etc.; and other alkylation catalysts. A preferred catalyst for use in the present invention is hydrofluoric acid.

The reaction may be carried out at pressures varying from atmospheric to as high as 1000 psi and higher, preferably about 125 to 220 psia and at residence times of 20 seconds to 5 minutes. The pressure is preferably sufficient to maintain the hydrocarbon reactant in their liquid phase.

In an alkylation reaction, involving the alkylation of isoparaffins with olefins, a substantial molar excess of isoparaffin to olefin is employed to provide a feed ratio in excess of about 1/1, usually about 4/1 to about 70/1 and preferably about 5/1 to about 20/1.

The reaction zone is preferably maintained under sufficient pressure to insure that the hydrocarbon reactants and the alkylation catalyst are in a liquid phase. The temperature of the reaction will vary with the reactants and with the catalyst employed, but generally ranges from between about $-40°$ F. to about $150°$ F. However, in the reaction of an isoparaffin, such as isobutane, with a $C_4$ olefin, such as butylenes, butene-1 and/or butenes-2, the reaction temperature is preferably between about $60°$ and about $100°$ F., and ideally about $90°$ F.

The catalyst settler vessel is comprised of an upper portion, an intermediate portion and a lower portion, which allows for separation of the reaction effluent from the alkylation reaction zone into (a) an upper hydrocarbon phase and (b) a lower catalyst phase containing acid-type catalyst and acid-soluble oil. The catalyst settler vessel contains a vertical baffle positioned at the point of introduction of the reaction zone effluent into the catalyst settler vessel, and downcomers, contacting points and separation trays positioned in the catalyst settler vessel so as to assure a means for sufficient separation of the reaction zone effluent and the rerun catalyst into a hydrocarbon phase and catalyst phase in the catalyst settler vessel.

Conventionally the hot rerun catalyst vapor from the HF catalyst rerun column is fed to the liquid hydrocarbon phase in the catalyst settler vessel. This vapor stream condenses in the liquid hydrocarbon yielding heat from the condensation of vapor which heats the liquid hydrocarbon.

The present invention prevents the upper hydrocarbon phase in the catalyst settler vessel from being pressurized above a desired maximum pressure. This higher pressure would require increased pressure on the recycled liquid HF catalyst which is charged to the catalyst settler vessel. The high pressure catalyst would then require higher pressures in the hydrocarbon fractionation system so that the recycled isobutane can flow in the alkylation reactor along with the higher pressure catalyst. The desired lower pressure saves construction costs on vessels, pumps, etc., and saves operating costs.

In order to maintain the desired pressure (and temperatures corresponding thereto) in the alkylation settler, the pressure control on the upper hydrocarbon liquid drawoff will manipulate the flow of hot hydrocarbon liquid from the upper drawoff in the catalyst settler vessel to the depropanizer, and the flow of cool hydrocarbon liquid from the lower hydrocarbon liquid drawoff in the catalyst settler vessel to the isostripper. The pressure controller is set to a desired pressure to be maintained in the upper portion of the catalyst settler vessel. As the pressure in the alkylation settler vessel increases (due to the hot rerun vapor entering the alkylation settler from the acid rerun vessel) the degree of closure of the lower drawoff valve emitting cool liquid hydrocarbon to the isostripper can be increased while the degree of opening of the upper drawoff valve emitting hot liquid hydrocarbon to the depropanizer is increased so as to increase the amount of hot liquid hydrocarbon to the isostripper. Thus operation of the upper or lower drawoff valve will shift that amount of heat necessary so as to remove heat from the catalyst settler vessel in order to maintain the desired pressure and temperature in the catalyst settler vessel. It is evident that too high of a pressure in the catalyst settler vessel adversely affects the alkylation operation, resulting in increased expenses for utilities, higher investment costs for equipment and loss of products due to relief valves opening as a result of excessive pressures.

Referring to the drawing, the isoparaffinic feed is introduced through line 4, the olefinic feed through line 2, recycle isobutane through line 6, and the catalyst feed through line 30. During normal operations, the isoparaffin feed, olefin feed and catalyst feed are introduced, as a mixture or individually at the lower end of the reaction zone 8. The reactor, coolers, etc. contain an inventory of catalyst such that the level of catalyst extends into the catalyst settler vessel 20. Therefore, the catalyst present in the alkylation system substantially exceeds in quantity the amount of hydrocarbon feed and hence constitutes a continuous phase in the system.

Effluent from the reaction zone 8 is discharged through line 10 to the catalyst settler vessel 20. In the catalyst settler vessel 20 the effluent is passed into a first separation zone having an upper and lower portion, and separated into a liquid alkylate product phase (a), located in the upper portion of the first separation zone, and a liquid catalyst phase (b), located in the lower portion of the first separation zone. The alkylate product phase is discharged through line 22 and line 49 to a depropanizer 50 (and a stripper 70) wherein isobutane and heavier hydrocarbons are removed from the propane and HF, and is charged to the isostripper 60 through line 52. Liquid HF catalyst is removed from the propane and is recycled to the system through line 42. The remainder of the alkylate product is then further processed in accordance with conventional practices. In the catalyst settler vessel 20, a first and second portion of the separated catalyst phase is withdrawn from the lower portion of the first separation zone. The first portion of the separated catalyst phase passes downwardly through line 31, to a cooler 32 and is recycled to the reaction zone 8 by means of line 30 for catalyst recycle. The second portion of the separated catalyst phase passes down through line 31 to a heater 33. The heated HF catalyst phase passes by means of line 34 to a rerun fractionator column 80. In the rerun fractionator column 80, the bottom stream comprising principally HF acid soluble oil, water, and some HF, is discharged through line 81. The overhead fraction from the rerun fractionator column 80, comprising hot rerun HF catalyst vapor and isoparaffin (mainly stripping vapors and reflux) is discharged through line 18. The hot rerun catalyst is recycled to the catalyst settler vessel 20 by means of line 18 to the alkylate product phase located in the upper portion of the first separation zone.

Use of the invention prevents the formation of high pressure in the catalyst settler vessel 20 due to the hot rerun catalyst entering the catalyst settler vessel by means of line 18. The desired pressure in the catalyst settler vessel is controlled by means of a pressure control device 28 attached to the alkylation settler vessel 20 so as to manipulate the flow of hot hydrocarbon liquid from an upper drawoff line 22 which is subsequently fed via line 49 to a depropanizer 50 and a stripper 70, and a cool lower drawoff line 24 which is fed via recontactor 40 to an isostripper 60. The pressure controller device 28 is set to the desired pressure to be maintained in the upper portion of the catalyst settler vessel 20. As the pressure in the catalyst settler vessel 20 increases (due to the increase of hot catalyst vapor from the rerun fractionator column 80 being condensed in the upper portion of the catalyst settler vessel 20) valve 100 is further opened while valve 101 is further closed so as to pass an increased amount of the hot hydrocarbon liquid to the isostripper 60 by means of line 26, and less cool hydrocarbon liquid by means of line 24. This procedure will shift heat to the isostripper 60 in order to remove heat from the catalyst settler vessel 20 so as to maintain the desired pressure and the temperature in the catalyst settler vessel 20. As the pressure in the catalyst settler vessel 20 decreases, valve 100 is further closed while valve 101 is further opened, so as to pass an increased amount of cool hydrocarbon liquid by means of line 24 to the isostripper 60 and less hot hydrocarbon liquid to the isostripper 60 by means of line 26. This procedure will add heat to the catalyst settler vessel 20 so as to maintain the desired pressure in the catalyst settler vessel 20.

EXAMPLE

Using the process of the invention shown in FIG. 1 the following flow rates and the following operating conditions in specific components of the system were calculated:

| Typical Flow Rates | |
|---|---|
| Feed Olefins, (2) B/D, (Contains $nC_4$, $iC_4$, $C_3$) | 11,500 |
| Feed Isobutane, (4) B/D, (Contains $nC_4$) | 8,224 |
| Recycle Isobutane, (6) B/D (95% $iC_4$, 5% $nC_4$) | 102,949 |
| HF Catalyst, (3) B/D, | 130,876 |
| Effluent From Reactor, (10) | |
| Total Hydrocarbon, B/D, | 121,021 |
| HF Catalyst, B/D, | 130,876 |
| Hydrocarbon, (22) B/D, (Saturated with HF), | 50,760 |
| Hydrocarbon, (24) B/D, (Saturated with HF), | 17,261 |
| Hydrocarbon, (26) B/D, (Saturated with HF), | 17,101 |
| Feed to Depropanizer, (49) B/D, | 33,659 |
| Feed to Isostripper, (59) B/D, | 87,362 |
| Alkylate, (61) B/D, | 14,089 |
| Propane, (71) B/D, | 1,440 |
| Normal Butane, (62) B/D, | 818 |
| HF Catalyst, (42) B/D, | 325 |
| HF Catalyst, (19) B/D, | 325 |
| Rerun Vapors, (18) (as Liquid B/D), to (A), | 1,400 |
| HF Vol %    45.0 | |
| $iC_4$ Vol %    50.0 | |
| $C_3$ Vol %    2.0 | |
| $nC_4$ Vol %    1.3 | |
| ASO Vol %    1.0 | |
| $H_2O$ Vol %    0.7 | |

| Operating Conditions in Specific Components | |
|---|---|
| Reactor (8): | |
| Pressure, psia, | 155 |
| Temperature, Outlet, °F., | 95 |
| HF/Total Hydrocarbon Volume Ratio, | 4:1 |
| $iC_4$/Olefin LV Ratio, (LV = Liquid Volume) | 13.0 |
| Separator (20): | |
| Pressure, psia, Top Section | 150 |
| Temperatures: °F., | |
| Inlet of Reactor Effluent | 95 |
| At Lower Drawoff (24) | 95 |
| At Upper Drawoff (22) | 130 |
| Recontractor (40): | |
| Pressure, psia, | 160 |
| Temperature (Top), °F., | 112 |

| Depropanizer (50): | |
|---|---|
| Pressure, psia, | 300 |
| Temperature (Top), °F., | 133 |
| Temperature (Bottom), °F., | 222 |
| Isostripper (60): | |
| Pressure, psia, | 120 |
| Temperature (Top), °F., | 138 |
| Temperature (Bottom), °F., | 325 |
| Stripper (70): | |
| Pressure, psia, | 330 |
| Temperature (Top), °F., | 136 |
| Temperature (Bottom), °F., | 148 |
| HF Rerun Column (80): | |
| Pressure, psia, | 160 |
| Temperature (Top), °F., | 290 |

Variation and modificaton are possible within the scope of the invention as described herein. One skilled in the art in possession of this disclosure having studied the same will understand that various engineering details of operation are necessarily omitted for sake of simplicity.

That what is claimed is:

1. Apparatus comprising:
    alkylation reactor means for producing alkylate product;
    acid catalyst settler means having an upper portion, an intermediate portion and a lower portion;
    means for withdrawing alkylate product from said alkylation reactor means and for providing alkylate product from said alkylation reactor means to a point of introduction in said intermediate portion of said acid catalyst settler means, said upper portion of said acid catalyst settler means being useful for containing a liquid hydrocarbon phase separated from alkylate product from said alkylation reactor means and said lower portion of said acid catalyst settler means being useful for containing a liquid catalyst phase separated from alkylate product from said alkylation reactor means;
    means for establishing a temperature gradient in said upper portion of said catalyst settler means, wherein temperature increases with height in said upper portion of said acid catalyst settler means;
    means for withdrawing a first liquid hyrocarbon stream from a first level in said upper portion of said acid catalyst settler means;
    means for withdrawing a second liquid hydrocarbon stream from a second level in said upper portion of said acid catalyst settler means, said first level being above said second level and said first liquid hydrocarbon stream being of a higher temperature than said second liquid hydrocarbon stream; and
    means for selectively varying the flow rate of said first liquid hydrocarbon stream and said second liquid hydrocarbon stream relative to each other in order to control a process variable in said upper portion of said acid catalyst settler means.

2. Apparatus in accordance with claim 1 wherein said means for establishing a temperature gradient in said upper portion of said acid catalyst settler means comprises:
    separating vessel means for separating acid catalyst from acid soluble oil;
    means for withdrawing an acid catalyst containing stream from said lower portion of said acid catalyst settler means and for providing said acid catalyst containing stream to said separating vessel means;
    means for withdrawing an overhead vapor stream containing acid catalyst from said separating vessel means, and means for introducing said overhead vapor stream containing acid catalyst from said separating vessel means into said upper portion of said acid catalyst settler means between said first level and said second level.

3. Apparatus in accordance with claim 1 wherein said upper portion, said intermediate portion and said lower portion of said acid catalyst settler means are included in a vessel and wherein said acid catalyst settler means additionally comprises:
    vertical baffle means positioned in said intermediate portion adjacent the point of introduction of alkylate product from said alkylation reactor means, and extending downwardly therefrom;
    a plurality of contacting means positioned within said vessel at different heights in said vessel for intimately contacting up flowing hydrocarbon liquid and down flowing acid catalyst liquid;
    a plurality of downcomers positioned within said vessel at different heights in said vessel, each downcomer being associated with a respective one of said plurality of contacting means, with the lowermost of said downcomers being remotely positioned from said vertical baffle means;
    wherein said first liquid hydrocarbon stream is withdrawn at a point above the uppermost one of said plurality of contacting means; and
    wherein said second liquid hydrocarbon stream is withdrawn at a point below the lowermost one of said plurality of contacting means.

4. Apparatus in accordance with claim 1 wherein said means for selectively varying the flow rate of said first liquid hydrocarbon stream and said second liquid hydrocarbon stream relative to each other in order to control a process variable in said upper portion of said acid catalyst settler means comprises:
    a first control valve operably located so as to adjust the flow rate in said first liquid hydrocarbon stream;
    a second control valve operably located so as to adjust the flow rate in said second liquid hydrocarbon stream;
    means for establishing a desired value for said process variable in said upper portion of said acid catalyst settler means; and
    means for manipulating said first control valve and said second control valve so as to maintain the actual value of said process variable in said upper portion of said acid catalyst settler means substantially equal to the desired value for said process variable.

5. An apparatus in accordance with claim 4 wherein said first liquid hydrocarbon stream is passed to a depropanizer, and said second liquid hydrocarbon stream is passed to an isostripper.

6. Apparatus in accordance with claim 4 wherein said process variable is temperature.

7. Apparatus in accordance with claim 4 wherein said process variable is pressure.

* * * * *